United States Patent
Ishii et al.

(10) Patent No.: US 9,445,773 B2
(45) Date of Patent: Sep. 20, 2016

(54) MEDICAL DIAGNOSTIC IMAGING APPARATUS

(71) Applicants: Hideaki Ishii, Nasushiobara (JP); Tomohiro Kawasaki, Otawara (JP)

(72) Inventors: Hideaki Ishii, Nasushiobara (JP); Tomohiro Kawasaki, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 320 days.

(21) Appl. No.: 13/730,009

(22) Filed: Dec. 28, 2012

(65) Prior Publication Data

US 2013/0116550 A1 May 9, 2013

Related U.S. Application Data

(63) Continuation of application No. PCT/JP2012/067347, filed on Jul. 6, 2012.

(30) Foreign Application Priority Data

Jul. 6, 2011 (JP) .................................. 2011-149869
Jul. 6, 2012 (JP) .................................. 2012-152273

(51) Int. Cl.
*A61B 3/16* (2006.01)
*A61B 5/103* (2006.01)
(Continued)

(52) U.S. Cl.
CPC ................ *A61B 6/12* (2013.01); *A61B 5/055* (2013.01); *A61B 6/461* (2013.01); *A61B 6/466* (2013.01);
(Continued)

(58) Field of Classification Search
CPC .............. A61B 5/06–5/068; A61B 19/5244; A61B 2019/5244–2019/5297; A61B 5/0059–5/0091; A61B 5/6852–5/6859; A61B 19/52–19/56

USPC ............... 600/424, 476–478, 101, 116, 115; 606/192, 191; 604/509, 103.06, 920, 604/96.01, 101.1
See application file for complete search history.

(56) References Cited

U.S. PATENT DOCUMENTS 7,853,308 B2 * 12/2010 Sauer et al. .................. 600/425
8,064,667 B2 * 11/2011 Kawasaki et al. ............ 382/128
(Continued)

FOREIGN PATENT DOCUMENTS

| CN | 1647759 A | 8/2005 |
|---|---|---|
| CN | 101516266 A | 8/2009 |

(Continued)

OTHER PUBLICATIONS

International Search Report and Written Opinion of the International Searching Authority issued Sep. 18, 2012, in PCT/JP2012/067347 (with English Translation of Category of Cited Documents).

(Continued)

*Primary Examiner* — John P Leubecker
*Assistant Examiner* — William Chou
(74) *Attorney, Agent, or Firm* — Oblon, McClelland, Maier & Neustadt, L.L.P

(57) ABSTRACT

Included are a storage unit for storing as first medical image information a three-dimensional image representing information about an inside of the subject; an image processor for generating a display image on the basis of the first medical image information and second medical image information; and a display for displaying the display image generated by the image processor. The image processor includes: a catheter position information detector for calculating a position of the balloon catheter C and detecting position information; and a balloon pressure-contact degree calculator for calculating a pressure-contact degree A of the tissues of the subject and a balloon b on the basis of the first medical image information and the position information.

7 Claims, 8 Drawing Sheets

(51) Int. Cl.
*A61B 5/117* (2016.01)
*A61B 1/00* (2006.01)
*A61B 1/04* (2006.01)
*A61B 6/12* (2006.01)
*A61B 6/00* (2006.01)
*A61B 5/055* (2006.01)
*A61B 18/14* (2006.01)
*A61F 2/24* (2006.01)
*A61B 5/06* (2006.01)
*A61B 18/00* (2006.01)

(52) U.S. Cl.
CPC ............... *A61B 6/50* (2013.01); *A61B 6/503* (2013.01); *A61B 6/5205* (2013.01); *A61B 6/5217* (2013.01); *A61B 18/1492* (2013.01); *A61B 5/06* (2013.01); *A61B 2018/0022* (2013.01); *A61B 2018/00357* (2013.01); *A61B 2018/00577* (2013.01); *A61B 2018/00636* (2013.01); *A61B 2034/104* (2016.02); *A61F 2/2433* (2013.01)

(56) References Cited

U.S. PATENT DOCUMENTS

| | | | |
|---|---|---|---|
| 8,155,416 B2* | 4/2012 | Nields et al. | 382/131 |
| 8,496,652 B2* | 7/2013 | Nguyen et al. | 606/28 |
| 8,538,106 B2* | 9/2013 | Ibarz et al. | 382/130 |
| 8,690,776 B2* | 4/2014 | Razzaque et al. | 600/437 |
| 2005/0033149 A1* | 2/2005 | Strommer et al. | 600/407 |
| 2005/0180544 A1* | 8/2005 | Sauer et al. | 378/195 |
| 2005/0240211 A1* | 10/2005 | Sporri et al. | 606/193 |
| 2005/0245807 A1 | 11/2005 | Boese et al. | |
| 2006/0106321 A1* | 5/2006 | Lewinsky et al. | 600/491 |
| 2006/0173288 A1* | 8/2006 | Eggers | 600/424 |
| 2006/0228012 A1* | 10/2006 | Masuzawa | 382/131 |
| 2008/0033417 A1* | 2/2008 | Nields et al. | 606/27 |
| 2008/0033418 A1* | 2/2008 | Nields et al. | 606/27 |
| 2008/0033419 A1* | 2/2008 | Nields et al. | 606/27 |
| 2008/0033420 A1* | 2/2008 | Nields et al. | 606/27 |
| 2008/0199059 A1* | 8/2008 | Eck et al. | 382/128 |
| 2008/0287803 A1* | 11/2008 | Li et al. | 600/466 |
| 2009/0016483 A1* | 1/2009 | Kawasaki et al. | 378/4 |
| 2009/0069672 A1* | 3/2009 | Pfister et al. | 600/424 |
| 2009/0118613 A1* | 5/2009 | Krugman et al. | 600/431 |
| 2009/0122953 A1* | 5/2009 | Imai | 378/5 |
| 2009/0137901 A1* | 5/2009 | Strommer et al. | 600/424 |
| 2009/0196480 A1* | 8/2009 | Nields et al. | 382/132 |
| 2009/0274271 A1* | 11/2009 | Pfister et al. | 378/62 |
| 2009/0306588 A1* | 12/2009 | Nguyen et al. | 604/96.01 |
| 2009/0312740 A1* | 12/2009 | Kim | A61M 25/1018 604/500 |
| 2010/0061603 A1* | 3/2010 | Mielekamp et al. | 382/128 |
| 2010/0111389 A1* | 5/2010 | Strobel et al. | 382/131 |
| 2010/0149183 A1* | 6/2010 | Loewke et al. | 345/424 |
| 2010/0157041 A1* | 6/2010 | Klaiman et al. | 348/77 |
| 2010/0160764 A1* | 6/2010 | Steinberg et al. | 600/407 |
| 2010/0160773 A1* | 6/2010 | Cohen et al. | 600/424 |
| 2010/0185087 A1* | 7/2010 | Nields et al. | 600/439 |
| 2010/0268067 A1* | 10/2010 | Razzaque et al. | 600/424 |
| 2010/0305479 A1* | 12/2010 | O'Dea | A61B 5/037 600/587 |
| 2011/0054395 A1* | 3/2011 | O'Dea | A61B 5/1076 604/97.02 |
| 2011/0091087 A1* | 4/2011 | Ibarz et al. | 382/131 |
| 2011/0130649 A1* | 6/2011 | Strommer et al. | 600/424 |
| 2011/0137156 A1* | 6/2011 | Razzaque et al. | 600/424 |
| 2011/0166407 A1* | 7/2011 | Sumanaweera et al. | 600/1 |
| 2011/0238082 A1* | 9/2011 | Wenderow et al. | 606/130 |
| 2012/0035642 A1* | 2/2012 | O'dea | A61B 5/1076 606/194 |
| 2012/0230565 A1* | 9/2012 | Steinberg et al. | 382/130 |
| 2012/0237105 A1* | 9/2012 | Mielekamp | 382/132 |
| 2012/0277525 A1* | 11/2012 | O'Dea | A61B 5/1076 600/104 |

FOREIGN PATENT DOCUMENTS

| | | |
|---|---|---|
| JP | 4-364833 A | 12/1992 |
| JP | 2007-282974 A | 11/2007 |
| JP | 2010-154945 A | 7/2010 |
| JP | 2010-193956 A | 9/2010 |
| JP | 2012-61086 A | 3/2012 |
| WO | WO 2008/036702 A2 | 3/2008 |

OTHER PUBLICATIONS

Chinese Office Action issued Aug. 29, 2014, in China Patent Application No. 201280001891.1 (with English and Japanese Translation).

* cited by examiner

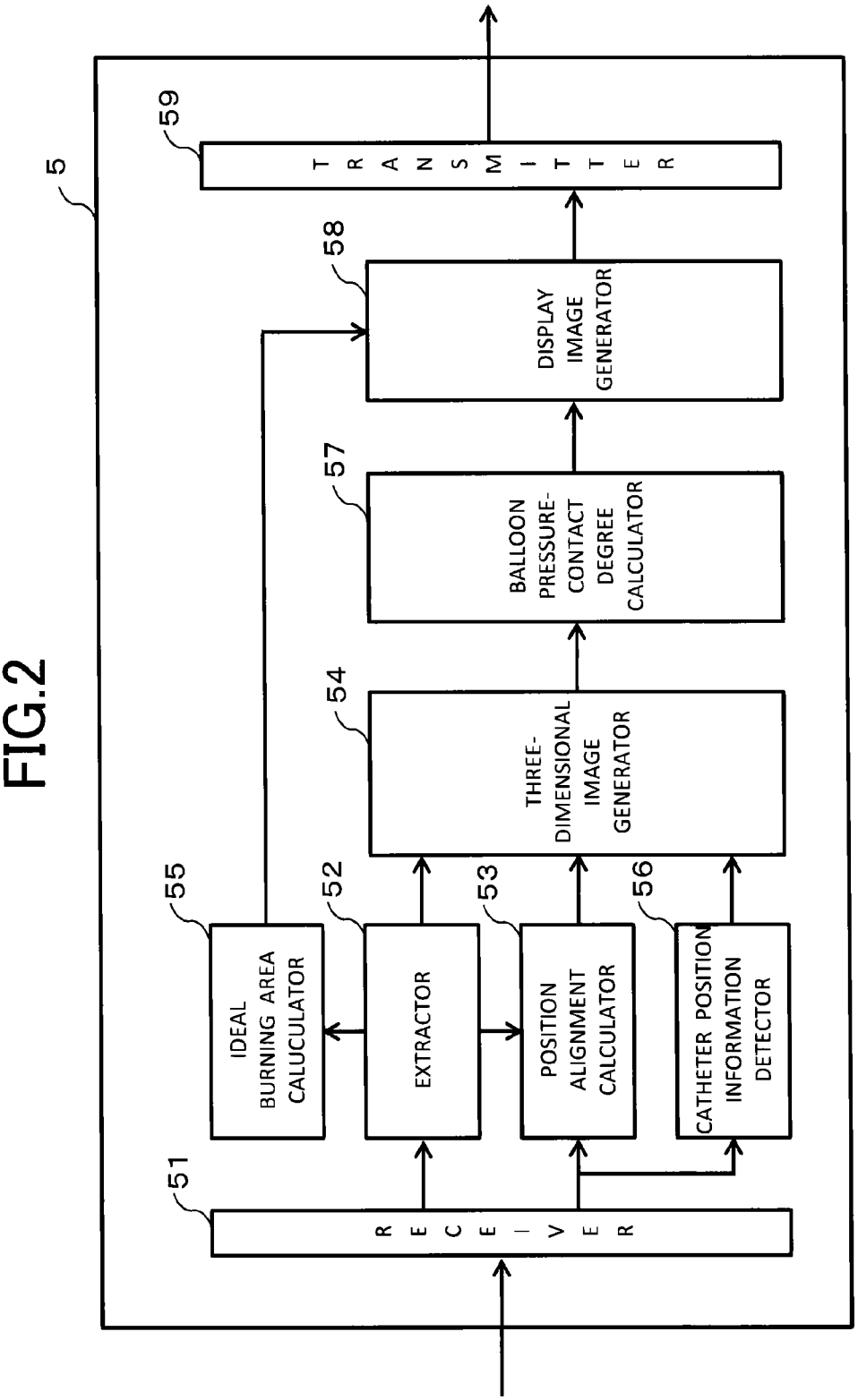

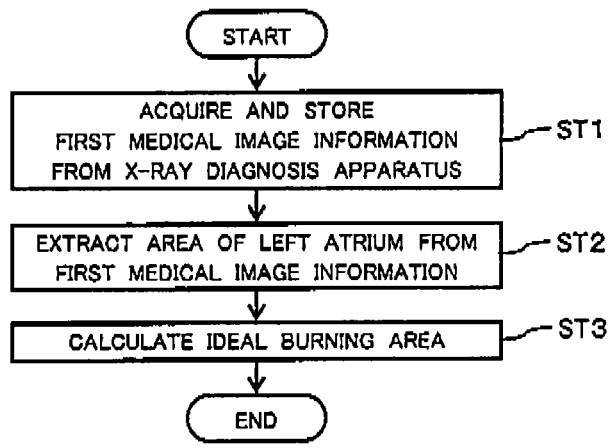
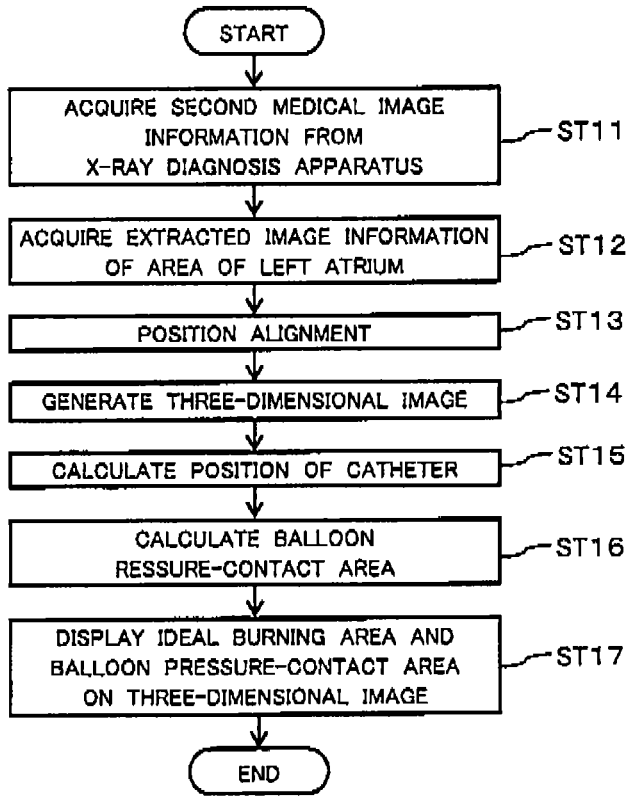

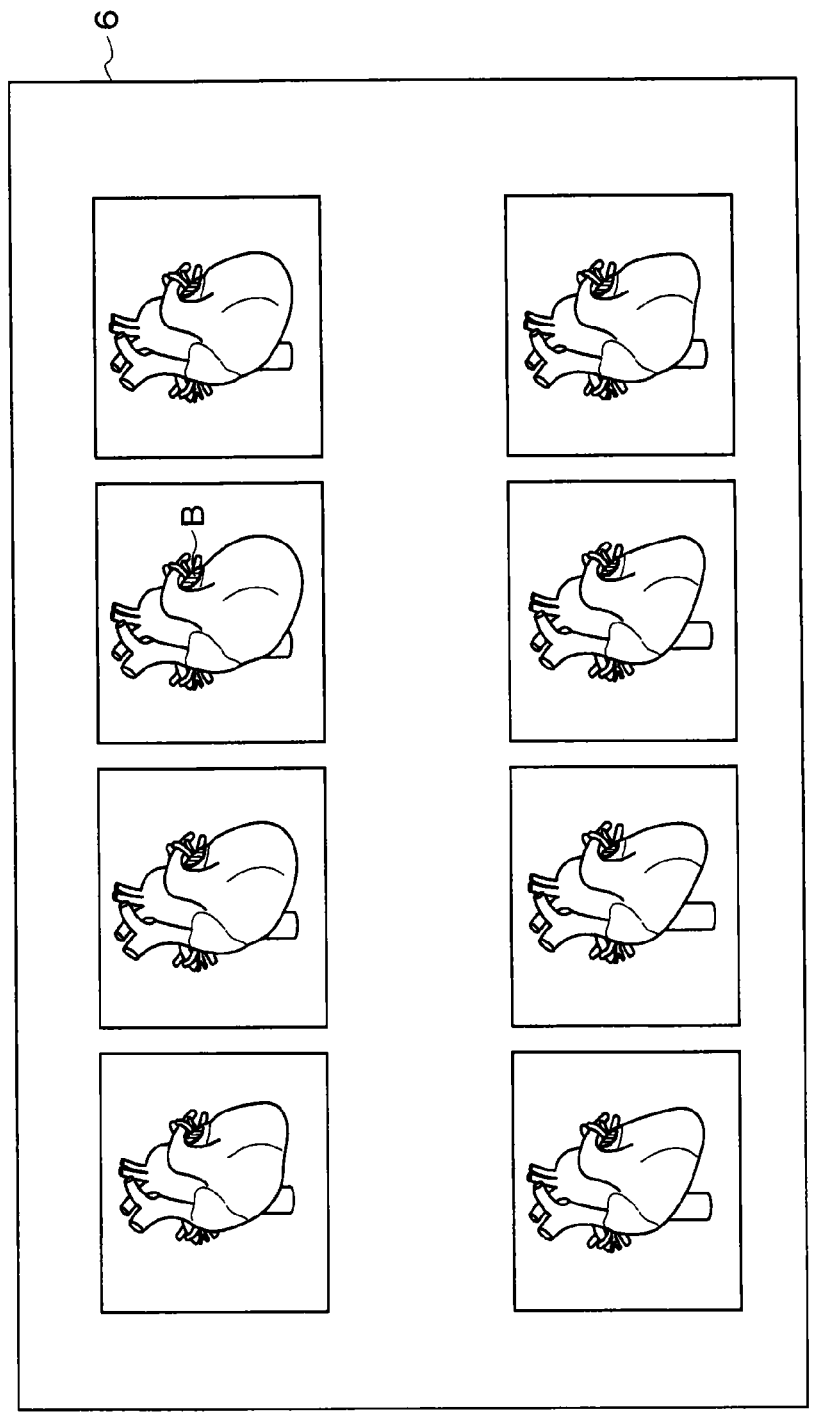

MEDICAL DIAGNOSTIC IMAGING APPARATUS

CROSS-REFERENCE TO THE RELATED APPLICATION

This application is a national phase of International Application No. PCT/JP2012/067347, which designates the United States of America and was filed on 6 Jul. 2012. The International Application No. PCT/JP2012/067347 is based on and claims the benefit of priority from Japanese Patent Applications No. 2011-149869, filed on 6 Jul. 2011, and No. 2012-152273, filed on 6 Jul. 2012; the entire contents of which are incorporated herein by reference.

FIELD

Embodiments of the present invention relate to a medical diagnostic imaging apparatus.

BACKGROUND

In these years, medical diagnostic imaging apparatuses have come into use, which are configured to collect information about the inside of a subject and to generate a medical image by imaging the inside of the subject on the basis of the collected information. For example, X-ray computed tomography (CT) apparatuses, magnetic resonance imaging (MRI) apparatuses and the like are the medical diagnostic imaging apparatuses. A generated medical image is displayed on, for example, a medical image display apparatus connected to the network.

Most cases of atrial fibrillation as a type of cardiac arrhythmia are considered to stem from the pulmonary veins of the left atrium of the heart. As one kind of treatment of atrial fibrillation, a so-called ablation treatment is carried out for the purpose of returning the flow of an electrical signal for causing the heart to beat to normalcy. In the ablation treatment, a part of the heart which disrupts the transmission of the electrical signal or its periphery is burned.

For the ablation treatment, a method using a balloon catheter has been employed in these years. The balloon catheter is originally used to restore the flow of blood in the coronary artery, peripheral blood vessel, or the like by treatment of dilating a stenosis site, blocked site or the like in the vascular lumen (see Japanese Patent Application Publication No. 2010-193956). However, in the ablation treatment, the balloon catheter is used for: heating a fluid filled in the balloon; and burning a target area or its periphery with heat. The ablation treatment method using the balloon catheter is advantageous over another ablation treatment method of directly burning a target area, in that an electric current for generating the heat for burning is not directly applied to the target area, and because the burning depth can be anticipated.

In a case where a balloon catheter disclosed in Japanese patent Application Publication No. 2010-193956 below described is used for the ablation treatment, specifically, the leading end of the catheter is inserted into the pulmonary vein of the left atrium of the heart, and the balloon is brought into pressure contact with the boundary between the pulmonary vein and the left atrium of the heart. Thereby, the boundary region is burned.

In this process, it is important that the balloon be completely brought into pressure contact with the tissues in the boundary region which needs to be burned (hereinafter referred to a "treatment target area"). To this end, the conventional ablation treatment judges that the balloon is in pressure contact with the treatment target area by: injecting the contrast medium from the front end of the catheter with the balloon in pressure contact with the treatment target area; and confirming by use of an X-ray machine that no portion of the contrast medium flows out of the pulmonary vein into the left atrium of the heart.

However, in the ablation treatment using the balloon, it is possible to check whether the balloon is in pressure contact with the periphery of the opening of the pulmonary vein of the left atrium of the heart, but it is impossible to check a pressure-contact degree such as a pressure contact area of the balloon as a whole. For this reason, it is impossible to exactly recognize a burning area in the ablation treatment.

In addition, in the ablation treatment, the amount of contrast medium applied to the subject is increased because whether or not the pressure contact occurs is checked by using the contrast medium in the ablation treatment. As a result, the ablation treatment may cause a harmful influence of raising the probability of the side-effects of the contrast medium compared with a non-ablation treatment.

BRIEF DESCRIPTION OF THE DRAWINGS

FIG. 2 is a block diagram showing an inner configuration of an image processor of the embodiment of the present invention.

FIG. 3 is a flowchart showing a preoperative flow of an ablation treatment, as using a balloon catheter, of the embodiment of the present invention.

FIG. 4 is a flowchart showing a mid-operative flow of the ablation treatment, as using a balloon catheter, of the embodiment of the present invention.

FIG. 12 represents the other example of the screen showing the other example of the displayed image in the embodiment of the present invention.

DETAILED DESCRIPTION

Figure 1:
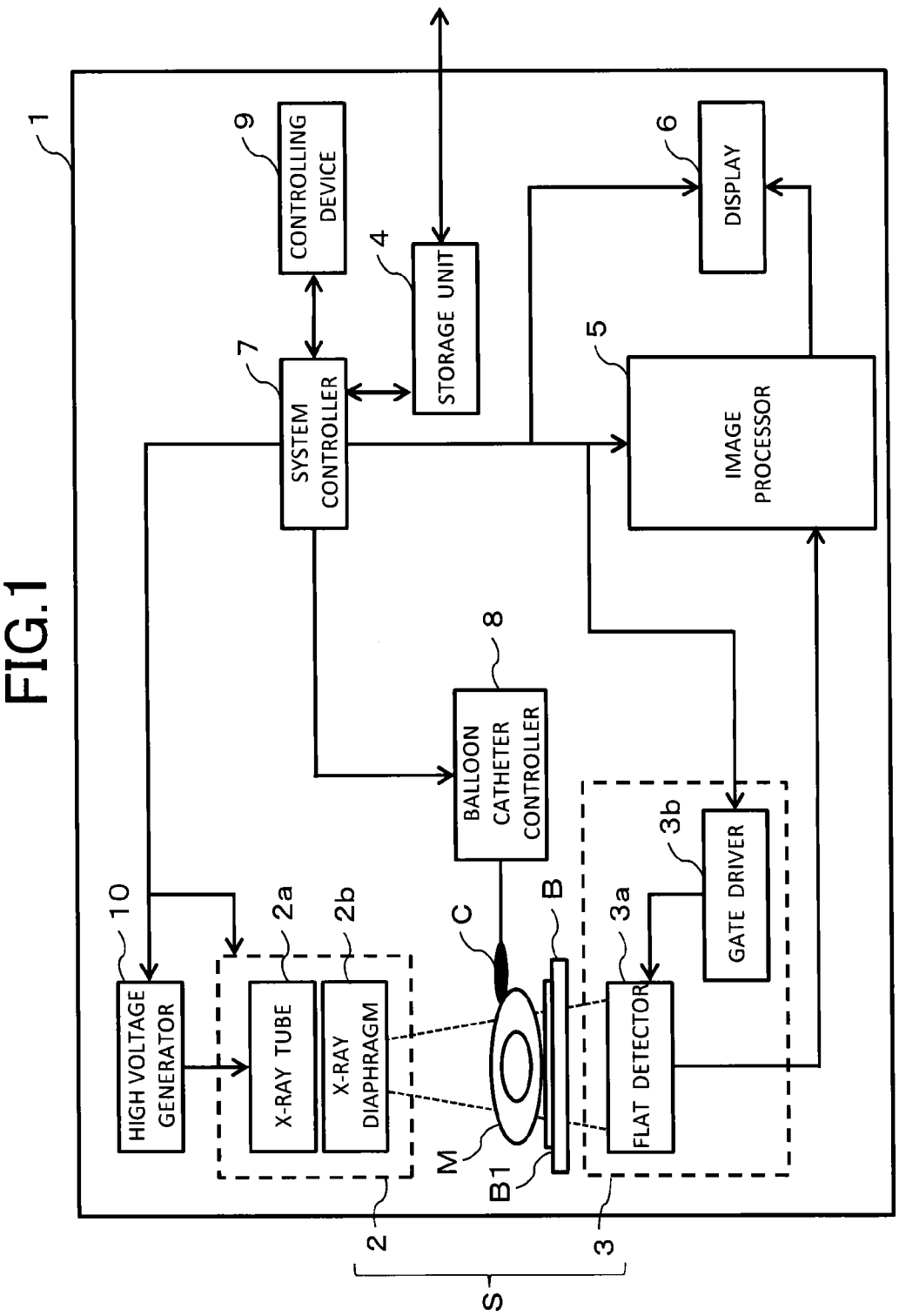
FIG. 1 is a block diagram showing an overall configuration of an X-ray diagnosis apparatus as an example of a medical diagnostic imaging apparatus of an embodiment of the present invention.

According to one embodiment of the present invention, a medical diagnostic imaging apparatus is configured to emit an X-ray from an X-ray generator, to detect the X-ray passing through a subject by use of an X-ray detector, and to display a detection result, the X-ray detector and the X-ray generator collectively forming a photographic system. The medical diagnostic imaging apparatus includes: a storage unit for storing as first medical image information a three-dimensional image, which represents information about the inside of the subject; an image processor for generating a display image on the basis of the first medical image information and second medical image information captured by photographing by the photographic system; and a display for displaying the display image generated by the image processor. The image processor includes: a catheter position information detector for calculating the position of a balloon catheter inserted into the body of the subject, and detecting position information of the balloon catheter; and a balloon pressure-contact degree calculator for calculating a pressure-contact degree of the tissues of the subject and the balloon on the basis of the first medical image information and the position information.

Various Embodiments will be described hereinafter with reference to the accompanying drawings.

Detailed descriptions will be hereinbelow provided for an embodiment of the present invention by referring to the drawings.

FIG. 1 is a block diagram showing an overall configuration of an X-ray diagnosis apparatus as an example of a medical diagnostic imaging apparatus 1 of the embodiment of the present invention. It should be noted that the following descriptions will be given by giving the X-ray diagnosis apparatus 1, which is used for an ablation treatment as using a balloon catheter, as an example of the medical diagnostic imaging apparatus.

The X-ray diagnosis apparatus 1 includes: a photographic system S formed from an X-ray generator 2 and an X-ray detector 3; a storage unit 4; an image processor 5; a display 6; and a system controller 7 for controlling the photographic system S, the storage unit 4, the image processor 5 and the display 6.

The X-ray diagnosis apparatus 1 further includes: a balloon catheter C used for a subject M during the ablation treatment; and a balloon catheter controller 8 for controlling the balloon catheter C under instructions from the system controller 7. For the ablation treatment, the following processes are carried out to expand or contract the balloon of the balloon catheter C inserted into a treatment target area inside the subject M, and then to burn the treatment target area. To put it specifically, various instructions concerning the burning and the like are sent to the system controller 7 through a controlling device 9 which is manipulated by a surgeon. On the basis of the instructions, the system controller 7 sends instructions to the balloon catheter controller 8.

For the photography, a photographic instruction is sent to the system controller 7 through the controlling device 9 which is manipulated by, for example, a clinical technician who intends to photograph an X-ray diagnosis image. On the basis of the instruction, the system controller 7 controls the various components of the X-ray diagnosis apparatus 1.

During the ablation treatment, the subject M lies supine on a bed B (a top board B1). It should be noted that FIG. 1 shows only the functions of the X-ray diagnosis apparatus 1 which are needed to explain the embodiment of the present invention. As a matter of course, various components and various mechanisms which are usually included in an X-ray diagnosis apparatus, such as a mechanism unit for driving the bed B and a mechanism controller for controlling this mechanism unit under instructions received from the system controller 7, are provided to the X-ray diagnosis apparatus 1, although omitted from the X-ray diagnosis apparatus 1 shown in FIG. 1.

The X-ray generator 2 includes: an X-ray tube 2a for emitting an X-ray to the subject M; and an X-ray diaphragm 2b for forming an X-ray cone beam from the X-ray which is emitted from the X-ray tube 2a. The X-ray tube 2a is a vacuum tube for generating the X-ray. The X-ray tube 2a generates the X-ray by: accelerating electrons, which are given off from a cathode (a filament), with high voltage supplied from a high voltage generator 10; and making the accelerated electrons collide against a tungsten anode. The X-ray diaphragm 2b is placed between the X-ray tube 2a and the subject M, and has a function of focusing the X-ray beam, which is emitted from the X-ray tube 2a, to an irradiation area of a predetermined size in the X-ray detector 3.

The X-ray detector 3 may be formed in various modes. The X-ray diagnosis apparatus 1 of the embodiment of the present invention uses a flat detector, because the detector is provided under the top board B1 of the bed B. This flat detector 3a includes multiple detection elements, and detects the X-ray passing through the subject M by use of the multiple detection elements. The detected X-ray is converted into an electrical signal by use of a converter which is not illustrated, and the resultant electrical signal is sent to the image processor 5 which will be described later. On the basis of an instruction from the system controller 7, a gate driver 3b drives the detection elements of the flat detector 3a.

For example, the storage unit 4 receives and stores information about the inside of the subject M, which is acquired by a modality (a medical image photographing system) such as an X-ray CT apparatus (hereinafter, such information about the inside will be referred to as "first medical image information" whenever deemed necessary) from the medical image photographing system. It should be noted that this storage unit 4 (the X-ray diagnosis apparatus 1) and the medical image photographing system provided separately are connected together through a communications network, which is not illustrated. Examples of the communications network include networks like a LAN (Local Area Network) set up in the hospital and the Internet. The communications standards used for this communications network N may be any standards such as the DICOM (Digital Imaging and Communication in Medicine).

The image processor 5 performs an image process on medical image information acquired by converting the X-ray which is detected by the X-ray detector 3 after emitted to the subject M and passing through the subject M (hereinafter, the medical image information thus acquired through the photographing by the X-ray diagnosis apparatus 1 will be referred to as "second medical image information" whenever deemed necessary). Furthermore, in the embodiment of the present invention, as described later, a three-dimensional (hereinafter, referred to as a "3D (3 dimensional)" whenever deemed necessary) image is generated by use of the first medical image information and the second medical image information, and an ideal burning area, a balloon pressure-contact area, and the like are displayed over the medical image. Descriptions will be later provided for an inner configuration of the image processor 5.

The display 6 displays a display image which is generated by the image processor 5. The display 6 further displays, for example, an input image and the like which are used to determine the photographing conditions, in addition to the display image.

The system controller 7 includes a CPU (Central Processing Unit) and the like which are not illustrated. On the basis of conditions and the like which are inputted or set by an operator using the controlling device 9, the system controller 7 collectively controls: the units such as the photographic system S, the image processor 5, the display 6 and the balloon catheter controller 8 which are included in the X-ray diagnosis apparatus 1; and the system as a whole.

The balloon catheter controller 8 controls the various components constituting the balloon catheter C. A balloon configured to expand and contract in accordance with the adjustment of the inner pressure of the balloon is provided to a catheter shaft of the balloon catheter C of the embodiment of the present invention. An inner cavity for supplying a fluid, which is used to adjust the inner pressure of the balloon, is provided inside the catheter shaft in the longitudinal direction of the catheter shaft. In addition, a heater for heating the fluid is provided inside the balloon. When the fluid inside the balloon is heated by heating this heater with the balloon being in pressure contact with the treatment target area, the area with which the balloon is in pressure contact is burned.

The controlling device 9 includes: input devices such as a key board, a joystick and a dial, as well as various switches, and the like through which the operator (for example, the surgeon and the clinical technician) inputs various operations. By manipulating the controlling device 9, the operator inputs information about the subject M, various commands, optimal conditions for emitting the X-ray to a photographic target area (for example, a tube voltage and tube current to be applied to the X-ray tube 2a, and the length of time for which the X-ray is emitted). In addition, the operator causes the ideal burning area, the pressure-contact area of the balloon and the treatment target area, and the like for the ablation treatment to be displayed on a display panel (the display 6).

FIG. 2 is a block diagram showing an inner configuration of the image processor 5 of the embodiment of the present invention. The image processor 5 includes a receiver 51, an area extractor 52, a position alignment calculator 53, a three-dimensional image generator 54, an ideal burning area calculator 55, a catheter position information detector 56, a balloon pressure-contact degree calculator 57, a display image generator 58 and a transmitter 59.

How these components constituting the inside of the image processor 5 work will be described when descriptions will be provided for the flow of the ablation treatment as using the balloon catheter C. In addition, the flow of the ablation treatment will be described in two processes of a "preoperative process" preceding the treatment and a "mid-operative process" in the treatment.

FIG. 3 is a flowchart showing the "preoperative" flow of the ablation treatment, as using the balloon catheter C, of the embodiment of the present invention. Furthermore, FIG. 4 is a flowchart showing the "mid-operative" flow of the ablation treatment, as using the balloon catheter C, of the embodiment of the present invention. Let us assume that the below-described ablation treatment is carried out to burn the periphery of the opening of a pulmonary vein of the heart, particularly the left atrium of the heart, of the subject M for the purpose of treating atrial fibrillation.

The flow of the preoperative process shown in the flowchart of FIG. 3 may be called a preparatory step for the ablation treatment. The storage unit 4 of the X-ray diagnosis apparatus 1 receives the information about a three-dimensional image (the first medical image information) from the medical image photographing system (the X-ray CT apparatus) not shown in FIG. 1 and connected to the X-ray diagnosis apparatus 1 through the communications network, and stores the information (ST1). The first medical image information is the one about the subject M undergoing the ablation treatment, and is photographed with the medical image photographing system in advance. The three-dimensional image can be generated from the first medical image information.

Subsequently, a process is performed for extracting an area of the left atrium of the heart, which is the target of the ablation treatment, from the first medical image information (ST2). The receiver 51 of the image processor 5 acquires the first medical image information from the storage unit 4 which has received and stored the first medical image information, and sends the first medical image information to the area extractor 52. This area extractor 52 extracts the area of the left atrium of the heart.

The extraction of the area of the left atrium of the heart is achieved by use of the following method, for example. First of all, the first medical image information and a general heart model beforehand stored in the area extractor 52 are position-aligned on the basis of, for example, the positions of blood vessels and the external shape of the heart. Information about the short-axial direction of the heart is recorded in this heart model. For this reason, on the basis of this information, the short-axial direction of the heart can be calculated from the first medical image information as well. It should be noted that although the foregoing descriptions have been provided on the assumption that the heart model is stored in the area extractor 52, the heart model may be stored, for example, in the storage unit or the like provided in the X-ray diagnosis apparatus 1.

Thereafter, a calculation is performed on the first medical image information in the calculated short-axial direction as if producing cross sections. On the cross sections identified as the result of the calculation, the boundary between the heart cavity and the inner wall of the heart is identified from the difference in CT values. Their reconstruction enables the area of the left atrium of the heart and the area of the opening of the pulmonary vein to be extracted from the first medical image information.

It should be noted that in this process, two states of the left atrium of the heart, namely a state in the terminal stage of its expansion and a state in the terminal stage of its contraction, are extracted. That is because if the ideal burning area and the balloon pressure-contact degree can be determined on the basis of the states in which the left atrium of the heart expands and contracts most, it is possible to prevent the balloon from becoming separated from the burning area in the heart which continues pulsating during the surgical operation (or to prevent its display from being disrupted), and according to provide a sufficient medical treatment.

Nevertheless, a basis of the image to be displayed on the display 6 is an image representing the state of the left atrium of the heart in the terminal stage of its expansion. That is because it is considered that if the balloon of the balloon catheter C is fully in pressure contact with the treatment target area during the terminal stage of the expansion, the treatment target area will not shift from the pressure-contact area of the balloon even when the heart (the left atrium of the heart) contracts.

Furthermore, as a planned burning range, the "ideal burning area" is calculated (ST3). This area is calculated by the ideal burning area calculator 55 on the basis of information about the area of the left atrium of the heart which is extracted by the area extractor 52. The area to be calculated as the "ideal burning area" is, for example, the one which is planned for the burning, and which is within the range of 5 mm from the periphery of the opening of the pulmonary vein with which the balloon is brought into pressure contact. The numerical value of the "5 mm" is a value generally accepted as the ideal burning range in the field of the ablation treatment as actually using the balloon catheter C.

It should be noted that any desired value may be set. The value should not be construed as proscribing the burning operation from being carried out beyond the value, that is to say, beyond the ideal burning area.

The preoperative process for the ablation treatment ends with this. During or after this process, the subject M lies supine on the bed B of the X-ray diagnosis apparatus 1, and medical instruments including the balloon catheter are prepared. Subsequently, the actual ablation treatment begins.

From now on, descriptions will be provided for the mid-operative process by use of the flowchart shown in FIG. 4 and the like. First of all, the image processor 5 receives the information about the radioscopic image of the subject M which has been photographed by the photographic system S of the X-ray diagnosis apparatus 1 (i.e., the second medical image information) by use of the receiver 51, and sends the information to the position alignment calculator 53 (ST11). At the same time, the position alignment calculator 53 acquires the image information about the area of the left atrium of the heart which has been extracted by the area extractor 52 (ST12). By this, the extracted image information about the area of the left atrium of the heart (i.e., the image information extracted from the first medical image information) and the second medical image information are collected to the position alignment calculator 53.

Subsequently, the position alignment calculator 53 performs a calculation in order to make the positions overlap each other on the basis of the two kinds of medical image information (ST13). An already-known technique may be used for this position alignment. Although not described in detail here, in a case where, for example, the position alignment is carried out for the area of the left atrium of the heart, the position alignment is achieved by using the bronchus and the heart contour as the reference. It is a matter of course that the position alignment may be achieved by use of any other method.

After the position alignment of the first medical image information and the second medical image information by the position alignment calculator 53, the resultant information is sent to the three-dimensional image generator 54, which generates the three-dimensional image (ST14). In this respect, an image as a basis of an image to be actually displayed on the display 6 is generated although, for example, the ideal burning area and the like are also actually displayed as described later.

Thereafter, the catheter position information detector 56 calculates the position of the balloon catheter C by use of the second medical image information (ST15). Because the second medical image information is the radioscopic image of the subject M, the position of the balloon catheter C can be identified in the second medical image information through the threshold process using the brightness value.

Instead, for example, another method of identifying the position (i.e., the three-dimensional coordinate position) of the balloon catheter C by use of a magnetic sensor may be employed to identify the position of the balloon catheter C. This method is the one in which the magnetic field generated by a magnetic field generator, which is grounded in the periphery of the subject M lying supine on the bed B, is sensed by the magnetic sensor attached to the balloon catheter C. The distance from the balloon catheter C to the magnetic field generator is calculated from the intensity of the magnetic field sensed by the magnetic sensor. The distance is calculated in all the three dimensions, and thus the exact position of the balloon catheter C is identified.

Information about the identified position of the balloon catheter C is sent to the three-dimensional image generator 54, which reflects the information over the three-dimensional image. To put it specifically, the radioscopic image and the three-dimensional image of the extracted area of the left atrium of the heart are position-aligned by the position alignment calculator 53 in advance. For this reason, the position coordinates of the balloon catheter C which move in real time can be reflected over the three-dimension image generated by the three-dimensional image generator 54.

It should be noted that the flowchart of FIG. 4 shows that the position of the catheter is calculated after the three-dimensional image is generated by the three-dimensional image generator 54. However, the calculation of the position of the balloon catheter C may be carried out, for example, in parallel with the position alignment step by the position alignment calculator 53.

Next, the pressure-contact degree is calculated to check whether or not the balloon of the balloon catheter C is in contact (i.e., pressure contact) with the inner wall of the area of the left atrium of the heart, i.e., the treatment target area. The pressure-contact degree is calculated by judging whether or not the pressure-contact takes place in various places on the basis of the relationship between the distance from the center portion of the balloon and the radius of the balloon (ST16).

In this respect, it should be noted that the "pressure-contact degree" is a concept meaning not only the amount of space (area) in which the balloon is in pressure contact with the treatment target area touched by the balloon, but also a judgment on whether or not the balloon touches the treatment target area. In other words, as the balloon becomes more strongly pressed against the treatment target area, the pressure-contact degree accordingly becomes higher, and the pressure-contact area becomes wider in the treatment target area. On the other hand, when the balloon starts to touch the treatment target area, the pressure-contact degree at which the balloon is in pressure contact with the treatment target area is low, so that an area in which the balloon is in pressure contact with the treatment target area is not recognized at this moment. In the following descriptions, the calculation of the pressure-contact degree means the calculation of the pressure-contact area, inclusive of the case where the balloon starts to touch the treatment target area.

Figure 5:
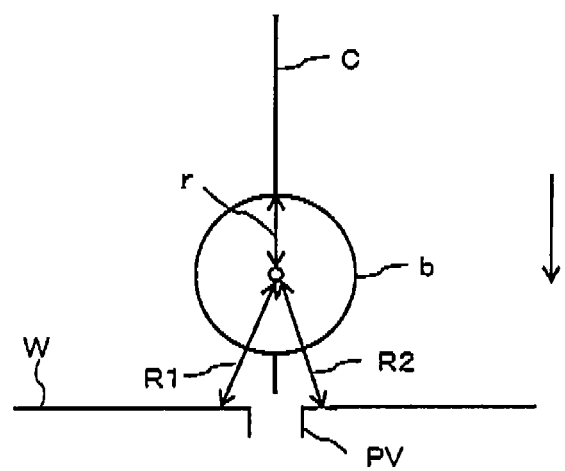
FIG. 5 is a conceptual diagram for how to calculate a pressure-contact area of a balloon and a treatment target area in the embodiment of the present invention.
Figure 6:
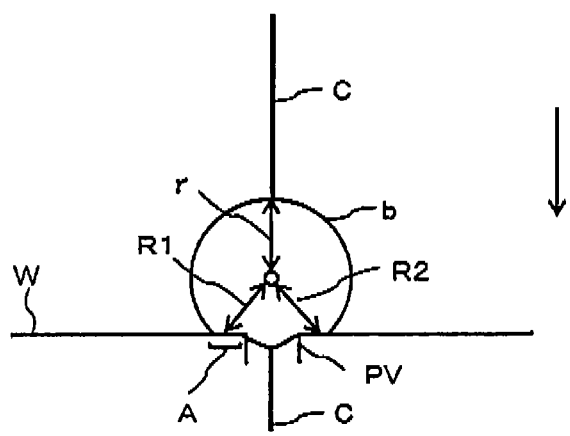
FIG. 6 is the other conceptual diagram for how to calculate the pressure-contact area of the balloon and the treatment target area in the embodiment of the present invention.
Figure 7:
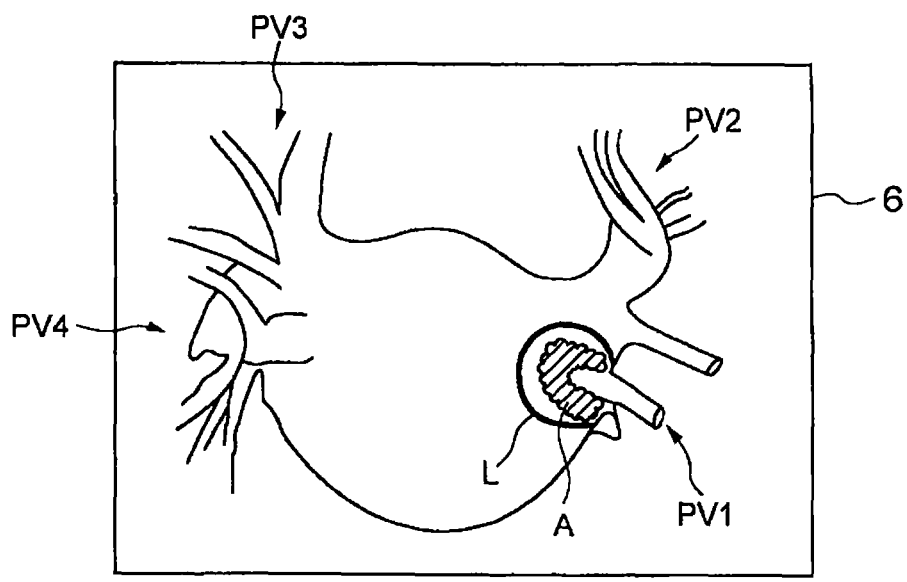
FIG. 7 represents an example of a screen showing an example of a displayed image in the embodiment of the present invention.

Specifically, the calculation is carried out as follows. FIG. 5 and FIG. 6 are conceptual diagrams for how to calculate the pressure-contact area where the balloon b included in the balloon catheter C is brought into pressure contact with the treatment target area in the embodiment of the present invention.

When the ablation treatment is carried out, the balloon catheter C (indicated with a continuous line in FIG. 5 and FIG. 6) is advanced to the treatment target area W (in a direction indicated with an arrow). In the ablation treatment, the balloon b needs to be brought into pressure contact with the treatment target area W for the purpose of burning the treatment target area W. As a result, the leading end portion of the balloon catheter C is partially inserted into the pulmonary vein PV. In FIG. 5, the leading end portion of the balloon catheter C has not reached such a state yet. In other words, the balloon b has not touched the treatment target area W yet.

In this respect, the radius of the balloon b is denoted by reference sign "r," and the distance from the center of the balloon b to the treatment target area W is denoted by reference sign "R." The calculation of the distance "R" is carried out within a range between previously-determined angles from the direction from the center of the balloon b to the leading end portion of the balloon catheter C. That is, for example, because when the distance R is calculated in the direction from the center of the balloon b to the place on the opposite side of the side on which the balloon catheter C is inserted, the pressure-contact area where the balloon b is brought into pressure contact with the treatment target area W cannot be found. Incidentally, these angles, and how finely the distance R should be calculated in what range within the range between the previously-determined angles, may be set as desired.

In the case shown in FIG. 5, the balloon b is not in contact with the treatment target area W. For this reason, the relationship between the radius r and the distance R from the center of the balloon b to the treatment target area W is one in which the distance R is greater than the radius r (r<R) (see R1 and R2). After calculating the distance R, the calculator calculates the pressure-contact area by comparing the distance R and the radius r. In the case of the state shown in FIG. 5, the area in which the balloon b is in pressure contact with the treatment target area W does not exist. Incidentally, as the distance R to be calculated, only R1 and R2 are shown for the sake of explanatory convenience.

On the other hand, FIG. 6 shows a state in which: the balloon catheter C is advanced in the direction indicated with an arrow; and the leading end portion of the balloon catheter C is partially inserted into the pulmonary vein PV. While in this state, the balloon b does not enter the pulmonary vein PV when the balloon catheter C is further advanced in the direction indicated with the arrow, because the radius r of the balloon b is greater than the inner diameter of the pulmonary vein PV. Accordingly, the balloon b comes into contact with the periphery of the opening of the pulmonary vein PV. As a result, the balloon b is in the state of being pressed against the treatment target area W in the direction indicated with the arrow. The contact area where the balloon b in the state of being pressed and the treatment target area W are in contact with each other is defined as a balloon pressure-contact area. This balloon pressure-contact area A spreads over the periphery of the opening of the pulmonary vein PV. The treatment target area W in the balloon pressure-contact area A is burned by heating the fluid in the balloon b by use of the heater provided in the same balloon b. In other words, the balloon contact-pressure area A is a burning area.

In order to judge whether or not the balloon b is in pressure contact with the treatment target area W, as described above, the balloon pressure-contact degree calculator 57 calculates the distance R, and thereafter compares the distance R with the radius r. In a case where the balloon b is in pressure contact with the treatment target area W (in a case shown in FIG. 6), the radius r has a larger value than the distance R (refer to R1 and R2). In other words, the radius r and the distance R are in a relationship of "r>R." For this reason, if a result like this is obtained as a result of the comparison, the balloon pressure-contact degree calculator 57 judges that the area representing this relationship is included in the balloon pressure-contact area A. As described above, the calculation of the balloon pressure-contact area A is achieved by making such a comparison at various points in the treatment target area W which spreads radially from the center of the balloon b.

It should be noted that, as shown in FIG. 6, the radius r and the distance R are equal to each other in an area in which the balloon b starts to touch the treatment target area W. The area of the boundary in such a case, that is to say, in the case where the balloon pressure-contact area A is calculated, is included in the concept of the pressure-contact degree, as described above.

However, in the case where, as described above, the radius r and the distance R are equal to each other, it is considered that: this state is the one in which only one point of the balloon b is in contact with the treatment target area W; and while in this state, no balloon pressure-contact area A is generated. Accordingly, it is considered that the balloon pressure-contact degree calculator 57 cannot calculate the balloon pressure-contact area A in such a case.

After calculating the balloon pressure-contact area A in the above-described manner, the balloon pressure-contact degree calculator 57 sends the information about the balloon pressure-contact area A to the display image generator 58. On the other hand, the information about the ideal burning area is sent from the ideal burning area calculator 55 to the display image generator 58 as well. In this respect, on the basis of the sets of information which are sent to the display image generator 58, the display image generator 58 generates a display image to be displayed on the display 6 (ST17). In addition to the targeted area where the ablation treatment is carried out (the left atrium of the heart in the embodiment of the present invention), a line L representing the ideal burning area and the balloon pressure-contact area A are displayed in the display image to be generated.

FIGS. 7 to 10 each represent an example of a screen showing an example of the display image in the embodiment of the present invention. The display image (displayed on the display 6) shown in each of FIGS. 7 to 10 is the one of the left atrium of the heart which is viewed from above (in the direction from the head toward the legs). Two left pulmonary veins (PV1, PV2) are shown in the right half of each drawing, while two right pulmonary veins (PV3, PV4) are shown in the left half of each drawing. It should be noted that: in each drawing, the display image of the heart (the left atrium of the heart) is schematically shown for the sake of explanation; and parts of the heart, which the explanation does not refer to, are omitted from each drawing.

The line L defining the ideal burning area is provided around the pulmonary vein PV1 in the area of the left atrium of the heart which is shown in each of FIGS. 7 to 10. In addition, the balloon pressure-contact area A (corresponding to the hatched area) is shown inside the line L defining the ideal burning area. In the case of the relationship between the balloon b and the treatment target area W (where the radius r<the distance R) which has been explained by use of FIG. 5, no balloon pressure-contact area A is displayed on the display screen because the balloon b is not in contact with the treatment target area W.

On the other hand, in the case where the relationship between the balloon b and the treatment target area W is as shown in FIG. 6 (where the radius r>the distance R), the balloon b is in contact with the target treatment area W. For this reason, the balloon pressure-contact area A is displayed on the display screen (see FIG. 7). As the pressure-contact degree becomes higher, the pressure-contact area A becomes wider. In addition, parts at which the contact starts are indicated with dots in the drawings. Accordingly, the boundary of the pressure-contact area A is displayed in a way that the dots seem to continuously form an arc. How large the dots should be displayed, or whether or not the parts at which the contact starts should be indicated with the dots in the first place can be set as desired.

It should be noted that although both the line L defining the ideal burning area and the treatment target area W are displayed in the following examples of the screen, only either the line L or the treatment target area W may be displayed as what should be displayed on the display image.

Figure 8:
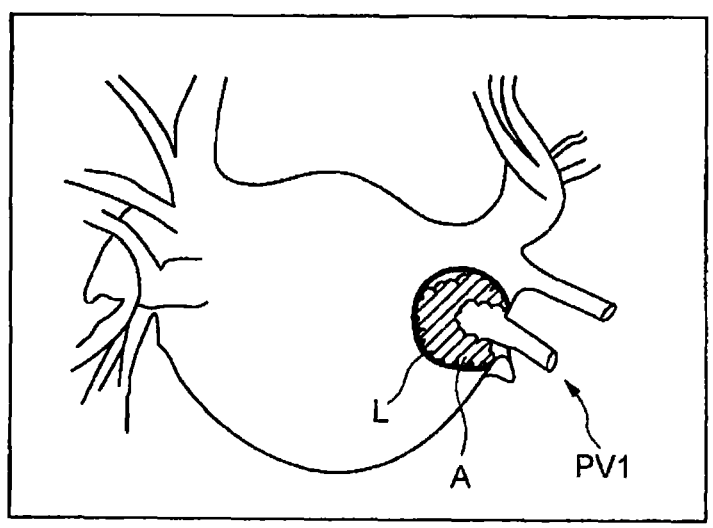
FIG. 8 represents another example of the screen showing another example of the displayed image in the embodiment of the present invention.

FIG. 8 shows the balloon pressure-contact area A which is almost the same as the ideal burning area defined by the line L. In the case shown in FIG. 8, therefore, it can be judged that the ablation treatment is being carried out in the ideal area.

Figure 9:
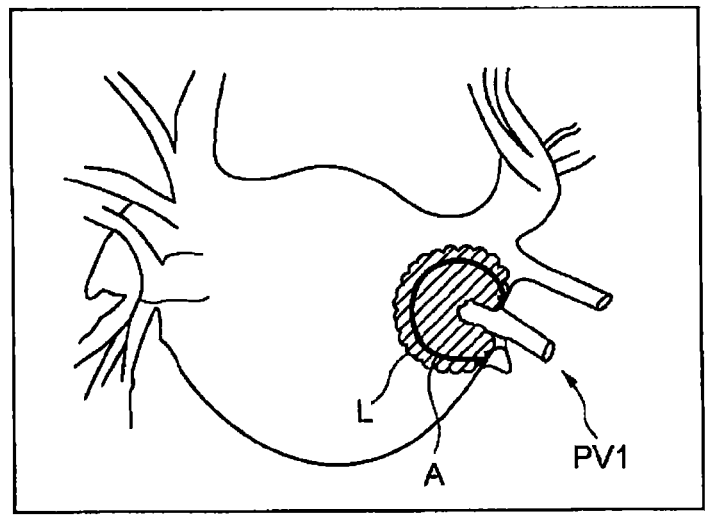
FIG. 9 represents another example of the screen showing another example of the displayed image in the embodiment of the present invention.

FIG. 9 shows the balloon pressure-contact area A which is beyond the ideal burning area defined by the line L. In this case, therefore, it can be judged that the ablation treatment is being carried out in a range wider than the ideal burning area.

Figure 10:
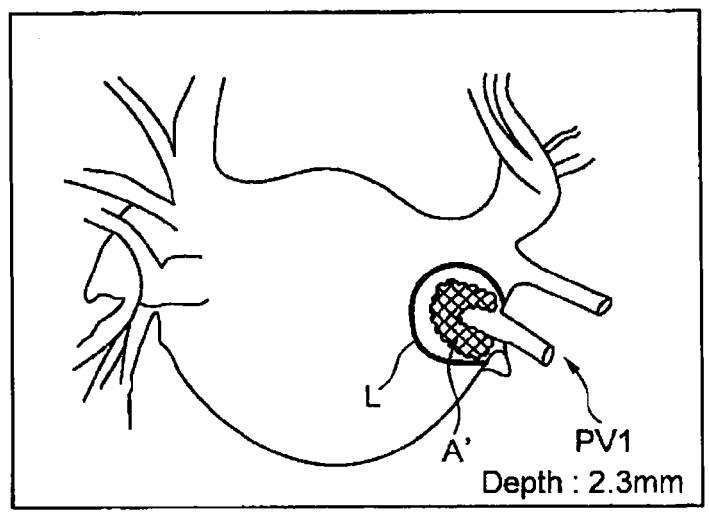
FIG. 10 represents yet another example of the screen showing yet another example of the displayed image in the embodiment of the present invention.

It should be noted that the below-mentioned contents may be additionally displayed on the display image. FIG. 10 represents an example of the screen showing an example of the display image in the embodiment of the present invention. The example of the screen shown in FIG. 10 is basically the same as the examples of the screen (shown in FIGS. 7 to 9) which have been explained, but has the following two features.

In FIG. 10, a balloon pressure-contact area A' is shown within the ideal burning area defined by the line L. However, FIG. 10 is different from, for example, FIG. 7 in terms of the way of displaying the balloon pressure-contact area A'. To put it specifically, as shown above, it is already understood that the predetermined relationship exists among the burning temperature, the burning time, and the melding-away depth of the pressure contact area of the balloon b. With this taken into consideration, the burning depth can be displayed on the screen on the basis of the time length when the balloon b is in contact with the treatment target area W. In FIG. 10, the balloon pressure-contact area A' which is equivalent to the burning area is shown in mesh. Furthermore, as the burning depth, the depth (reading "Depth: 2.3 mm") is shown in the right lower corner in the screen. A constitution may be employed in which: the length of time of the contact is measured by, for example, a timer provided in the X-ray diagnosis apparatus 1; and information about the length of time and the like are supplied to the image processor 5.

It should be noted that the burning area may be displayed by using any display (showing) method, such as highlighting the area in a particular color or flickering the area, instead of the meshing of the area. In addition, the display of the burning depth may be achieved by employing a method of showing the burning depth by displaying, for example, color scales or the like, which indicates a relationship between the depth and displayed colors, on the screen, instead of the numerical value as shown in FIG. 10.

Figure 11:
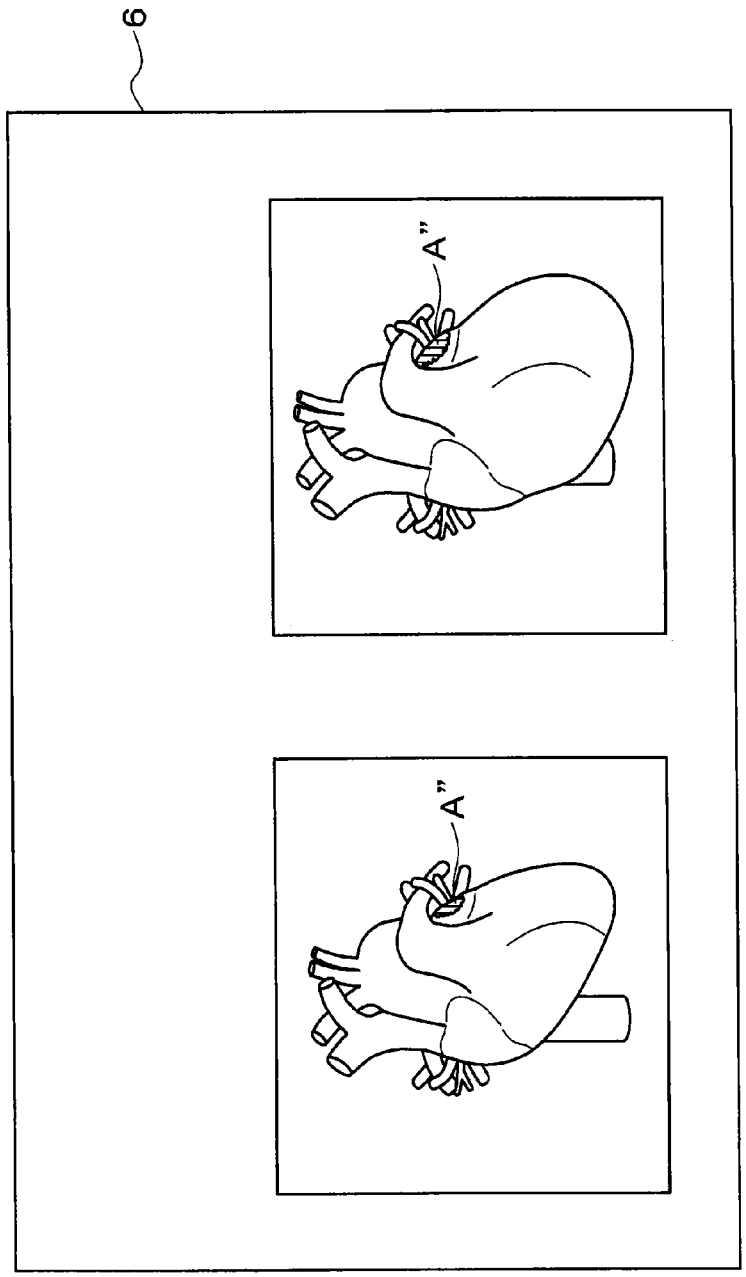
FIG. 11 represents still another example of the screen showing still another example of the displayed image in the embodiment of the present invention.

Moreover, it may be considered that: as the display image, the organ as a whole, inclusive of the target area, is displayed; and the pressure-contact area and the line defining the ideal burning area are shown on the display. FIG. 11 represents an example of the screen showing an example of the display image, which displays the heart from the front, in the embodiment of the present invention. It should be noted that: this drawing also schematically shows the display image of the heart for the sake of explanation; and parts of the heart, to which the explanation does not refer, are omitted from the drawing. Furthermore, the line L defining the range of the ideal burning area may be displayed as described above, although the display of the line L is omitted from the drawing.

As the display image, two images are shown in the display 6. In the figure, one image representing the terminal stage of the contraction of the heart and one image representing the terminal stage of the expansion of the heart are shown. The image representing the terminal stage of the contraction is shown in the left half of FIG. 11, while the image representing the terminal stage of the expansion is shown in the right half of the FIG. 11. As mentioned above, the basis of the display is the image representing the terminal stage of the expansion. The reason why the image representing the terminal stage of the contraction is additionally shown is that when the case where the heart becomes largest due to the pulsation and the case where the heart becomes smallest due to the pulsation are displayed in juxtaposition, the differences in the pressure-contact degree (pressure-contact area A'') can be contrasted.

In addition, although the generating of the display image has been described by using the example where the information about the three-dimensional image is used as the first medical image information (see FIGS. 7 to 10), information about a four-dimensional image, for example, may be instead used as the first medical image information. In this case, the line defining the ideal burning area or the balloon pressure-contact area can be displayed as the display image by position-aligning the four-dimensional image with the radioscopic images which are photographed by the X-ray diagnosis apparatus 1 in real time (along the time axis). The displaying of the four-dimensional image makes it possible to further deepen the understanding by the surgeon which carries out the ablation treatment.

FIG. 12 represents the other example of the screen showing the other example of the displayed image in the embodiment of the present invention. In FIG. 12, the states of the heart pulsation are displayed in the display 6 in the chronological order. In addition, a pressure-contact area B is shown in each example of the screen. It can be learned that the size of the pressure-contact area B changes in conjunction with the change in the size of the heart due to the pulsation.

Furthermore, although all the states of the heart pulsation are displayed in FIG. 12 in the chronological order, the states of the heart pulsation may be displayed one after another (i.e., cinematically displayed) like a motion picture. Otherwise, a display scheme may be selected in which: only one of the images is displayed in a larger size; and the rest of the images are displayed as auxiliary ones in a different size. In other words, the display mode, the display layout and the like, as well as the display method may be set as desired.

As described above, when the ablation treatment as using the balloon catheter is carried out, the displaying of the pressure-contact degree (the burning area) on the display image depending on the necessity makes it possible for the surgeon to accurately and securely recognize the pressure-contact area (the burning area), and enables the pressure-contact area (the burning area) to be recognized without using the contrast medium, as well as can provide the medical diagnostic imaging apparatus which reduces stress on the subject who is the target of the treatment.

The foregoing descriptions have been provided for the method of generating the display image in the image processor within the medical diagnostic imaging apparatus (the X-ray diagnosis apparatus). The process by this image processor may be achieved by: designing and constructing software; and installing the software into, for example, a workstation or the like. In this case, the workstation, the modality for supplying the first medical image information and the modality for supplying the second medical image information are connected together through the single communications network. On the basis of the first medical image information and second medical image information which are collected to the workstation, the process is performed for displaying the ideal burning area, the balloon pressure-contact area and the like.

Moreover, although the foregoing descriptions have been provided by giving the X-ray diagnosis apparatus as an example of the medical diagnostic imaging apparatus 1, the X-ray CT apparatus, the magnetic resonance imaging apparatus and the like, for example, are included in the category of the medical diagnostic imaging apparatus 1 as well.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic imaging apparatus configured to emit an X-ray from an X-ray generator, to detect the X-ray passing through a subject by use of an X-ray detector, and to display a detection result, the X-ray detector and the X-ray generator collectively forming a photographic system, the apparatus comprising:
    a storage for storing as first medical image information a three-dimensional image representing information about an inside of the subject, and a position of a treatment target area in a three-dimensional space;
    an image processor for generating a display image on the basis of the first medical image information and a second medical image information captured by photographing by the photographic system; and
    a display for displaying the display image generated by the image processor, wherein
    the image processor configured to
        calculate a position of a balloon catheter for ablation treatment inserted into the body of the subject, and detect position information of the balloon catheter;
        compare a distance from center of the balloon catheter to the treatment target area with radius of the balloon catheter to obtain an area of the balloon catheter in contact with the treatment target area, and
        display the area of the balloon catheter in contact with the treatment target area on the display.

2. The medical diagnostic imaging apparatus of claim 1, wherein the image processor is further configured to:
    extract a treatment target area on the basis of the first medical image information;
    perform a calculation for position alignment in order to generate a three-dimensional image as a basis of the display image by use of the second medical image information and the first medical image information representing the treatment target area which is extracted;
    generate the three-dimensional image by overlaying the first medical image information and the second medical image information each other in a position calculated by the position alignment; and
    calculate an ideal burning area for the balloon catheter in the treatment target area; and
    generate a display image of the ideal burning area alone, or together with a pressure-contact area in the treatment target area, over the display image.

3. The medical diagnostic imaging apparatus of claim 1, wherein the image processor calculates the position of the balloon catheter on the basis of a brightness value included in the second medical image information, and identifies the position in the display image.

4. The medical diagnostic imaging apparatus of claim 1, wherein
    the image processor calculates a radius of the balloon and a distance from the center of the balloon to a part included in a treatment target area on the basis of the detected position information of the balloon catheter, and
    if the radius of the balloon is greater than the distance from the center of the balloon to the part included in the treatment target area, the image processor determines the part as being within a balloon pressure-contact area by calculation.

5. The medical diagnostic imaging apparatus of claim 1, further comprising
    a system controller for controlling the storage, the image processor and the display, said system controller configured to measure a length of time after the balloon starts to get into pressure contact with a treatment target area, and
    upon reception of information about the length of time from the system controller, the image processor generates a display image of a burning depth of a burning area, the burning depth being preset in accordance with the length of time.

6. The medical diagnostic imaging apparatus of claim 1, wherein in a case where a treatment target area is the heart, the first medical image information acquired by the storage includes information representing a terminal stage of contraction of the heart and information representing a terminal stage of expansion of the heart.

7. The medical diagnostic imaging apparatus of claim 1, wherein the first medical image information acquired by the storage is four-dimensional information, and is generated as the display image by the image processor on the basis of the second medical image information along a time axis.

* * * * *